United States Patent
Wolfe et al.

(10) Patent No.: US 9,339,498 B2
(45) Date of Patent: May 17, 2016

(54) SEDATING AND IMMOBILIZING NON-DOMESTICATED MAMMALS

(71) Applicant: Wildlife Laboratories, Incorporated, Windsor, CO (US)

(72) Inventors: Lisa L. Wolfe, Fort Collins, CO (US); Michael W. Miller, Fort Collins, CO (US); William R. Lance, Fort Collins, CO (US); David K. Smith, Windsor, CO (US)

(73) Assignee: Wildlife Laboratories, Inc., Windsor, CO (US)

( * ) Notice: Subject to any disclaimer, the term of this patent is extended or adjusted under 35 U.S.C. 154(b) by 0 days.

(21) Appl. No.: 14/644,602

(22) Filed: Mar. 11, 2015

(65) Prior Publication Data

US 2015/0290186 A1    Oct. 15, 2015

Related U.S. Application Data

(60) Provisional application No. 61/977,454, filed on Apr. 9, 2014.

(51) Int. Cl.
| | | |
|---|---|---|
| *A61K 31/497* | (2006.01) | |
| *A61K 31/485* | (2006.01) | |
| *A61K 31/4174* | (2006.01) | |
| *A61K 9/00* | (2006.01) | |
| *A61K 31/496* | (2006.01) | |

(52) U.S. Cl.
CPC ............. *A61K 31/485* (2013.01); *A61K 9/0019* (2013.01); *A61K 31/4174* (2013.01); *A61K 31/496* (2013.01)

(58) Field of Classification Search
CPC ..................................................... A61K 31/484
USPC ..................................................... 514/253.01
See application file for complete search history.

(56) References Cited

U.S. PATENT DOCUMENTS

| | | | |
|---|---|---|---|
| 5,972,932 A | 10/1999 | Benvenga et al. | |
| 7,795,263 B2 * | 9/2010 | Lance ................... | A61K 9/0019 514/253.01 |

OTHER PUBLICATIONS

Rauser et al. STN Abstract of Veterinarstvi (2007), vol. 57, No. 2, pp. 72-75.*
Girard et al.:Veterinary Anaesthesia and Analgesia vol. 37, Issue 1, pp. 1-6, Jan. 2010.*
Will nalbuphine replace butorphanol? Rauser, P. et al. Faculty of Veterinary Medicine of the Veterinary and Pharmaceutical University in Brno. Veterinarstvi [veterinary medicine], Pharmacological influencing of tumor diseases. Mutliple myeloma, casuistics. Jan. 2007, year 57. Translation to English, 6 pages.

* cited by examiner

*Primary Examiner* — Nizal Chandrakumar
(74) *Attorney, Agent, or Firm* — Santangelo Law Offices, P.C.

(57) ABSTRACT

Non-domesticated mammalian animals are sedated and immobilized by injecting an effective amount of pharmaceutically effective combination of nalbuphine hydrochloride and medetomidine hydrochloride into the animal from a dart. Azaperone tartrate may also be included, if desired.

6 Claims, 2 Drawing Sheets

SEDATING AND IMMOBILIZING NON-DOMESTICATED MAMMALS

CROSS REFERENCE TO RELATED APPLICATION

This application claims the benefit of U.S. provisional application Ser. No. 61/977,454, filed Apr. 9, 2014, for an invention titled "Sedating and Immobilizing Non-Domesticated Mammals," which was invented by the inventors hereof and which is assigned to the assignee of the present invention.

FIELD OF THE INVENTION

This invention relates to sedating and immobilizing non-domesticated free-ranging and confined mammals with a new and improved combination of pharmaceutically effective nalbuphine hydrochloride and medetomidine hydrochloride (NalMed) or nalbuphine hydrochloride, medetomidine hydrochloride and azaperone tartrate (NalMed-A), using a relatively small volumetric quantity suitable for accurate and safe delivery remotely by a dart.

BACKGROUND OF THE INVENTION

Large non-domesticated mammals are typically sedated or immobilized for reasons of medical examination or treatment, or for reasons of physiologic or morphologic study, herd health assessment, or animal relocation, or as matter of protecting public safety. The non-domesticated nature of the animals makes it impossible to approach or safely handle them without sedation or immobilization, even in captive environments such as zoological parks or animal preserves. Performing any procedure that produces pain is also impossible unless the animal is heavily sedated or provided with analgesia, because the animal will resist such a procedure, even if the animal is substantially confined or physically restrained.

The sedating or immobilizing agent should be medically safe for administration to the animal. Mortality is usually not an acceptable outcome of any medical or scientific study, examination or relocation activity. The sedating and immobilizing agent should not create undesirable physiological side effects, such as significant body temperature variations, hyperthermia, muscle rigidity and excitement, among other things. Significant muscle rigidity, despite sedation and immobilization, makes it impossible, difficult or dangerous to conduct a treatment or examination or to move the animal.

Animal and public safety also involves achieving complete or near-complete reversibility of the sedated and immobilized state, without a prolonged recovery time. Since a free-ranging non-domesticated animal will usually be released into the natural environment after sedation or immobilization, the animal should be able to respond to flight-invoked stimulus and to protect itself naturally, both of which are compromised if the animal remains partially sedated. A prolonged sedated condition creates a risk of death or injury from its natural predators or from failing to successfully negotiate natural environmental hazards, such as cliffs and bodies of water, or a potential threat to public safety.

It is important to be able to administer the sedating or immobilizing agent from a remote distance by a dart. Non-domesticated animals cannot be approached for injection by hand without fleeing. The flight distance which a non-domesticated animal will tolerate varies with the species and the environment. Darts are used under such circumstances to inject the animal from a remote distance of up to about 70 meters. Shooting or projecting the dart should be accomplished with reasonable accuracy to assure that the dart will inject the drug into the muscle mass of a shoulder or hind quarter of the animal. Impacting the dart in a bony area such as the rib cage or lower extremity will not allow the needle of the dart to penetrate sufficiently to deliver the full dose of the sedating or immobilizing agent. To ensure an adequate projection distance and good accuracy in aiming its placement, the dart must be relatively small. A relatively small dart is capable of carrying only a relatively small volumetric quantity of the sedating or immobilizing agent. Consequently, a small volume of the agent must have adequate potency to accomplish the desired effect.

The factors involved in successfully immobilizing non-domesticated free-ranging and confined mammals are described in U.S. Pat. No. 7,795,263. This US patent describes an advantageous pharmaceutical combination of butorphanol tartrate, azaperone tartrate and medetomidine hydrochloride (BAM), which is effective in achieving desirable effects and reducing undesirable effects when immobilizing many different species of animals.

One disadvantage associated with BAM, and most other known immobilizing pharmaceutical agents for non-domesticated animals, is that these agents utilize opioids or other types of drugs which involve a significant risk of human abuse. Because of their potential for human abuse, governmental drug regulatory agencies, such as the United States Drug Enforcement Administration (DEA), impose strict regulatory controls on the use and conditions of use of such pharmaceutical agents, including strict penalties for violation of these regulations. For example, governmental regulations require a Doctor of Veterinary Medicine to administer or oversee the administration of these drugs to animals. The regulations also require a precise and complex accounting of the amount of each drug administered and the amount of each drug kept on hand. The regulations also impose strict requirements on keeping the drugs secure from theft, which practically means that the drugs must be kept in locked safes.

Strict governmental regulations may be more readily complied with in a zoological park which typically has a veterinarian available to administer or oversee the administration of the drugs. Furthermore, the animals are kept in a relatively small and confined geographical area where the veterinarian may quickly and conveniently access the animal. A zoological park usually possesses the necessary safe and other physical facilities for safekeeping the drugs and keeping records of their administration. However, in those circumstances where the non-domesticated mammals are free-ranging in government or privately-owned wildlife preserves, or in herds in very large confinement areas, the task of overseeing and caring for the animals is typically undertaken by trained technicians and biologists who are not veterinarians. These non-veterinarians need to sedate or immobilize animals in the wild or in open areas under circumstances where it is not practical or possible logistically to call for the services of a veterinarian and then wait for his or her arrival before the immobilizing drug is administered. Under such circumstances, or under circumstances where the regulatory compliance and administration burden is so substantial as to be prohibitory from a practical standpoint, there is no completely satisfactory unscheduled (not subject regulatory control) immobilizing agent or combination which can be administered to non-domesticated mammals across a wide range of species.

SUMMARY OF THE INVENTION

The sedating and immobilizing pharmaceutical combination of this invention is formed by a synergistic combination of pharmaceutically effective ingredients nalbuphine hydrochloride and medetomidine hydrochloride (NalMed) or nalbuphine hydrochloride, medetomidine hydrochloride and azaperone tartrate (NalMed-A). These drugs are not regulated by governmental drug enforcement agencies, or are so lightly regulated that the invention may be administered by non-veterinarians and without encountering substantially burdensome record-keeping and safe-keeping requirements. Despite avoiding the use of more potent regulated drugs, the present invention is nonetheless effective and safe in sedating and immobilizing free-ranging and captive non-domesticated mammals. Immobilization is accompanied by adequate muscle relaxation and a good plane of sedation and pain relief which greatly facilitates medical, physiologic, morphologic, herd assessment or relocation activities. The invention requires only a moderate induction time, thereby reducing the distance that a free-ranging animal will travel after administration and before immobilization, thereby reducing the amount of time required to locate and care for the sedated and immobilized animal. The invention creates recumbency which is usually required for accomplishing the examination or medical activity. Reversal of the sedation is accomplished by administering common and readily available antagonists. Recovery after administering the antagonist is relatively rapid and smooth, thereby reducing the death or injury risks to the animal from natural hazards such as predators, cliffs and bodies of water. The present invention is sufficiently potent in small volumetric quantities to permit reliable, accurate and remote delivery by a dart, while still achieving and maintaining the beneficial effects in relatively large animals, for example animals having a weight greater than 20 kg. By formulation from components which are not presently considered as having potential for human abuse, the invention is considerably easier to use from an administrative burden standpoint, while still yielding effectiveness comparable to strictly regulated drugs. Further still, the use of the unscheduled components makes the invention the first known satisfactorily performing analgesic and immobilizing drug combination which is not a controlled substance and which thus substantially eliminates the current administrative burden of using such an agent.

The invention describes the first known use of nalbuphine hydrochloride in any combination used for successfully achieving clinically acceptable immobilization and anesthesia of non-domesticated mammals.

One aspect of the present invention relates to an injectable sedating and immobilizing pharmaceutical combination for non-domesticated mammalian animals of a variety of species comprising pharmaceutically effective ingredients of NalMed or NalMed-A.

Another aspect of the invention involves a method of sedating and immobilizing a non-domesticated mammalian animal by injecting a combination of the liquid pharmaceutically effective ingredients of NalMed or NalMed-A into a non-domesticated mammalian animal from a dart which is shot or projected from a position substantially separated from the animal.

A further aspect of the invention relates to a method of making an injectable sedating and immobilizing drug for non-domesticated mammalian animals, comprising combining predetermined pharmaceutically effective quantities of solutions of nalbuphine hydrochloride and medetomidine hydrochloride or nalbuphine hydrochloride, medetomidine hydrochloride and azaperone tartrate.

Additional features of the invention relate to using a volumetric quantity of NalMed or NalMed-A of no greater than 3 milliliters to effectively, accurately and safely sedate and immobilize non-domesticated animals of weight greater than 20 kg. A preferred relative weight ratio relationship of the pharmaceutically effective ingredients for NalMed is in the range of 14-55 mg/ml of nalbuphine hydrochloride and 5-22 mg/ml of medetomidine hydrochloride, and for NalMed-A is in the range of 14-55 mg/ml of nalbuphine hydrochloride, 5-22 mg/ml of medetomidine hydrochloride and 5-22 mg/ml of azaperone tartrate. Preferably, the approximate relationship is 40 mg/ml of nalbuphine hydrochloride and 10 mg/ml of medetomidine hydrochloride in NalMed and 40 mg/ml of nalbuphine hydrochloride, 10 mg/ml of medetomidine hydrochloride and 10 mg/ml of azaperone tartrate in NalMed-A. The sedating and immobilizing effects of NalMed are substantially reversed by injecting antagonists.

In NalMed-A, the azaperone tartrate enhances some aspects of the physiological response of some species of non-domesticated animals to sedation and immobilization, or diminishes the induction time, or produces a state of mild tranquilization after recovery, or all of the above, if desired by the user. Azaperone tartrate is not a controlled substance, so NalMed-A is not a controlled substance. Adding the azaperone tartrate does not increase the effective volumetric dose above 3 milliliters. Antagonists effectively reverse the immobilizing effects of NalMed-A.

Other aspects and features of the invention, and a more complete appreciation of the present invention, as well as the manner in which the present invention achieves the above described and other improvements and benefits, is obtained by reference to the following detailed description of presently preferred embodiments taken in connection with the accompanying drawings, which are briefly summarized below, and by reference to the appended claims.

DETAILED DESCRIPTION

Figure 1:
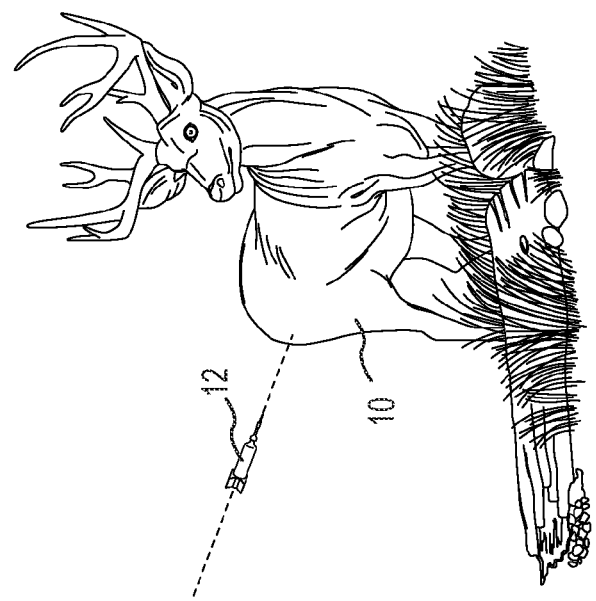
FIG. 1 is an illustration of remotely delivering a sedating and immobilizing agent according to the present invention to a non-domesticated animal with a dart.
Figure 1:

The present invention involves sedating and immobilizing free-ranging and captive non-domesticated mammalian animals 10, such as a deer shown in FIG. 1, by administering an sedating and immobilizing combination of effective ingredients of nalbuphine hydrochloride and medetomidine hydrochloride referred to herein as "NalMed." NalMed is delivered remotely, preferably by a dart 12 as shown in FIG. 1. If circumstances permit, NalMed may be administered by hand injection. NalMed is formulated as discussed below in conjunction with FIG. 2. NalMed is preferably supplied as a liquid which is ready to inject.

To administer the NalMed as shown in FIG. 1, the weight of the animal 10 is estimated and a liquid volumetric quantity of 3 ml or less of NalMed is loaded into a conventional dart 12. The dart 12 is shot or projected and its needle enters a muscle mass of the animal 10, preferably in a shoulder or a hind quarter. Once injected, the NalMed is absorbed from the intramuscular injection site into the bloodstream of the animal. After a short induction time, the NalMed sedates and immobilizes the animal. The animal collapses in a recumbent position and enters into a plane of sedation with relaxed muscles, thereby allowing medical, physiologic, morphologic herd-assessment or relocation activities to be performed on the animal.

While sedated, the animal shows no adverse side effects which are significantly outside of the accepted norms for anesthetic parameters. The heart rate, respiration rate, rectal temperature, arterial blood pressure, and hemoglobin saturation level and other vital signs are within normally-accepted anesthesia limits. Parameters evaluating the quality of the induction, maintenance of the plane of sedation, muscle relaxation, recovery, and overall procedure are observed as favorable.

At the conclusion of the procedures and tests, the effect of the NalMed is reversed by administering an antagonist formed from naltrexone hydrochloride, tolazoline hydrochloride and/or atipamezole hydrochloride. Recovery is observed as smooth and rapid, and the animal relatively quickly achieves a level of consciousness and responsiveness sufficient to guard against and negotiate natural adversities such as predators, water bodies and cliffs. Significant post recovery side effects are not apparent. A slightly sedated state may be maintained for a short time by antagonizing only the medetomidine hydrochloride.

Figure 2:
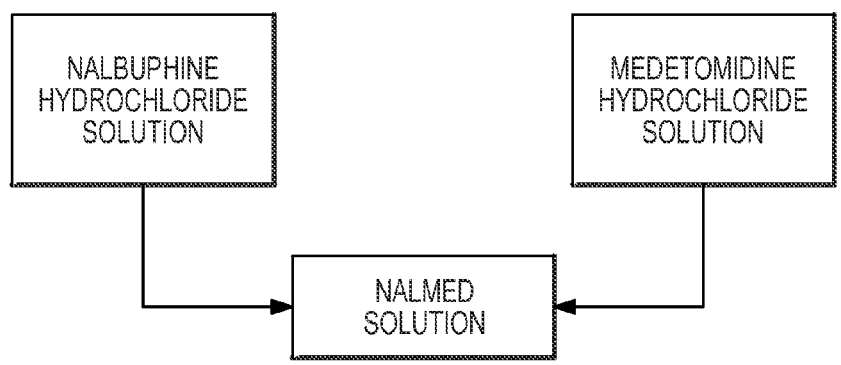
FIG. 2 is a diagram illustrating formulation of a pharmaceutically effective combination of nalbuphine hydrochloride and medetomidine hydrochloride (NalMed) as a sedating and immobilizing agent, in accordance with the present invention.

NalMed is prepared from solutions of nalbuphine hydrochloride and medetomidine hydrochloride, as shown in FIG. 2. The nalbuphine hydrochloride solution is preferably concentrated to 40 mg/ml and the medetomidine hydrochloride solution is preferably concentrated to 10 mg/ml. The resulting total solution creates a total liquid volume of 10 ml, in which there exits 400 mg of nalbuphine hydrochloride and 100 mg medetomidine hydrochloride.

Sedating and immobilizing a larger non-domesticated animal weighing greater than 20 kg may require a higher drug concentration, which means that a greater amount of NalMed is dissolved in a lesser amount of sterile water. In some circumstances, it may be desirable to have a greater amount of injection volume, which is achieved by increasing the amount of sterile water compared to the amount of NalMed. Under typical circumstances, the usual concentration is 50 mg of total NalMed components per ml of sterile water, although acceptable concentrations range from 20 mg/ml to 80 mg/ml.

Variations in the relative proportion of nalbuphine hydrochloride and medetomidine hydrochloride are possible, although the preferred relative weight ratio relationship of the pharmaceutically effective ingredients is about 40 mg/ml of nalbuphine hydrochloride and about 10 mg/ml of medetomidine hydrochloride. However, other suitable relative weight ratio relationships are in the range of 14-55 mg/ml of nalbuphine hydrochloride and 5-22 mg/ml of medetomidine hydrochloride.

The relative proportions of the nalbuphine hydrochloride and medetomidine hydrochloride may be varied in accordance with the response characteristics of the species and the size of animal to which NalMed is administered. Typical doses range from approximately 0.30 mg of total NalMed components per kilogram of animal weight to approximately 1.30 mg of total NalMed components per kilogram of animal weight. It is the responsibility of the user to make the ultimate determination of the dose.

Reversal of the sedation and immobilization created by NalMed is achieved by hand injection of an antagonist formed by naltrexone hydrochloride and tolazoline hydrochloride followed in about five minutes within injection of atipamezole hydrochloride. Naltrexone hydrochloride and tolazoline hydrochloride are effective in reversing the effect of nalbuphine hydrochloride. Naltrexone hydrochloride is preferably administered at approximately 2 times the nalbuphine hydrochloride dose in terms of milligrams of nalbuphine hydrochloride per kilogram of animal weight. Tolazoline hydrochloride is preferably administered at approximately 2 mg per kilogram of animal weight. Atipamezole hydrochloride is effective in reversing the effect of medetomidine hydrochloride, and is preferably administered at approximately 3-5 times the medetomidine hydrochloride dose in terms of milligrams of medetomidine hydrochloride per kilogram of animal weight.

A variation of NalMed also includes the pharmaceutically effective ingredient azaperone tartrate. The combination of nalbuphine hydrochloride, medetomidine hydrochloride and azaperone tartrate is referred to herein as "NalMed-A." Azaperone tartrate is included when it is desired to improve muscle relaxation, to improve induction time and consistency, to provide sustained tranquilization, or to relieve anxiety in non-domesticated animals being immobilized and handled.

The normal body and physiological parameters are observed as within satisfactory limits for typical sedation and immobilization when NalMed by itself is employed, without using NalMed-A. However, NalMed-A may prove beneficial when the ambient environmental temperature or other environmental conditions indicate that it is desirable to enhance a body or physiological parameter. Regardless, NalMed-A offers the opportunity for slight modification of the body or physiological parameters or response characteristics, should a user desire to do so.

Azaperone tartrate is not a controlled substance. Consequently, including azaperone tartrate in the pharmaceutically effective combination does not subject NalMed-A to any greater level of regulation than NalMed, thereby offering the same practical and logistical advantages of using NalMed-A as occur from using NalMed.

Figure 3:
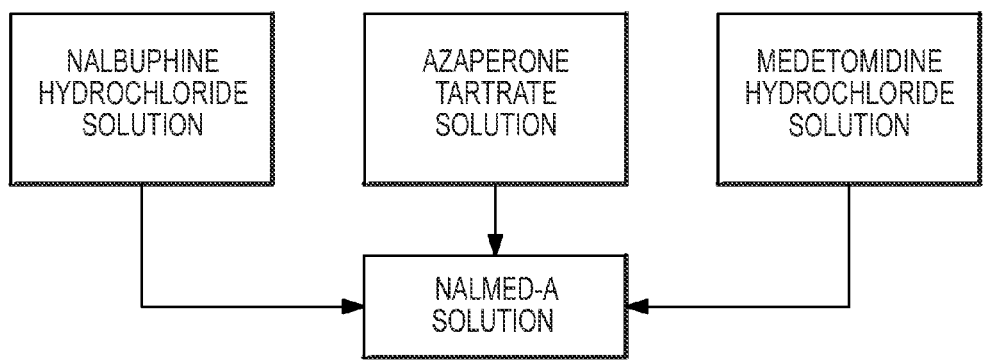
FIG. 3 is a diagram illustrating the formulation of a pharmaceutically effective combination of nalbuphine hydrochloride, medetomidine hydrochloride and azaperone tartrate (NalMed-A) as a sedating and immobilizing agent, in accordance with the present invention.

NalMed-A is prepared from solutions of nalbuphine hydrochloride, azaperone tartrate and medetomidine hydrochloride, as shown in FIG. 3. The nalbuphine hydrochloride solution is preferably concentrated to 30-50 mg/ml, the azaperone tartrate is preferably concentrated to 10 mg/ml, and the medetomidine hydrochloride solution is preferably concentrated to 10 mg/ml. The resulting total solution creates a total liquid volume of 10 ml, in which there exits 300-500 mg of nalbuphine hydrochloride, 100 mg of azaperone tartrate, and 100 mg medetomidine hydrochloride.

Sedating and immobilizing a larger non-domesticated animal may require a higher concentration of NalMed-A, which means that a greater amount of NalMed-A is dissolved in a lesser amount of sterile water. In some circumstances, it may be desirable to have a greater amount of injection volume, which is achieved by increasing the amount of sterile water compared to the amount of NalMed-A. Under typical circumstances, the usual concentration is 60 mg of total NalMed-A components per ml of sterile water, although acceptable concentrations range from 20 mg/ml to 80 mg/ml.

Variations in the relative proportion of nalbuphine hydrochloride, azaperone tartrate and medetomidine hydrochloride are possible, although the preferred relative weight ratio relationship of the pharmaceutically effective ingredients is about 30-50 mg/ml of nalbuphine hydrochloride, about 10 mg/ml of azaperone tartrate and about 10 mg/ml of medetomidine hydrochloride. However, other suitable relative weight ratio relationships are in the range of 14-55 mg/ml of nalbuphine hydrochloride, 5-22 mg/ml azaperone tartrate and 5-22 mg/ml of medetomidine hydrochloride.

The relative proportions of the nalbuphine hydrochloride, azaperone tartrate and medetomidine hydrochloride may be varied in accordance with the response characteristics of the species and the size of animal to which NalMed-A is administered. Typical doses range from approximately 0.30 mg of total NalMed-A components per kilogram of animal weight to approximately 1.30 mg of total NalMed-A components per kilogram of animal weight. It is the responsibility of the user to make the ultimate determination of the dose.

Reversal of the sedation and immobilization created by NalMed-A is achieved by hand injection of an antagonist formed by naltrexone hydrochloride, tolazoline hydrochloride and/or atipamezole hydrochloride, in the same proportions as described above for NalMed. Despite there being no antagonist for azaperone tartrate, satisfactory recovery is nevertheless observed. A slightly sedated state may be maintained for a short time after sedation and immobilization by antagonizing only the medetomidine hydrochloride.

The utility and effectiveness of the NalMed and NalMed-A in sedating and immobilizing certain species is discussed in the following Examples.

Example 1

NalMed and NalMed-A were first tested on adult Rocky Mountain elk (*Cervus elaphus nelsoni*). A nalbuphine hydrochloride dosage of about 0.3 mg/kg was used in both NalMed and NalMed-A. NalMed and NalMed-A were both effective in immobilizing the adult elk. NalMed (40 mg/ml nalbuphine hydrochloride and 10 mg/ml medetomidine hydrochloride) was dosed at 1.8-2.0 ml, and NalMed-A (40 mg/ml nalbuphine hydrochloride, 10 mg/ml azaperone tartrate and 10 mg/ml medetomidine hydrochloride) was dosed at 1.8-2.0 ml. Dose volumes that included about 80 mg nalbuphine hydrochloride tended to yield shortest inductions. A mean induction time of 6.8 min occurred with NalMed-A, and a mean induction time of 7.7 minutes occurred with NalMed.

For recovery, 50 mg naltrexone hydrochloride and 600 mg tolazoline hydrochloride were administered intramuscularly (IM) about 5 min in advance of 100 mg atipamezole hydrochloride (divided 25 mg intravenously [IV] and 75 mg IM). Administration in this manner proved effective. Mild sedation or tranquilization can be extended beyond recovery by antagonizing only the medetomidine hydrochloride component, or by using NalMed-A.

All elk immobilized with NalMed or NalMed-A were observed daily for over two weeks for any after effects. No adverse after effects were observed.

Example 2

Five bighorn sheep (*Ovis canadensis*) under fenced management were successfully immobilized by the administration of NalMed. The five sheep had an average weight of 72.2 kg. Each animal received 1 ml of NalMed. The 1 ml dose contained 40 mg nalbuphine hydrochloride and 10 mg medetomidine hydrochloride. The average dose rate was 0.55 mg/kg of nalbuphine hydrochloride and 0.14 mg/kg medetomidine hydrochloride. The average time to first effect was 4.8 minutes. The average time to safe approach was 9 minutes.

Sedation was reversed with a combination of atipamezole hydrochloride, tolazoline hydrochloride, and naltrexone hydrochloride, as in Example 1. All animals completely recovered to standing in 8 to 16 minutes. Significantly, no supplemental oxygen was required, since all of these animals maintained oxygen saturation levels above 79%.

Example 3

Eight white-tailed deer (*Odocoileus virginiansus*) in a fenced enclosure under management were administered NalMed-A by remote injection dart. Six of the eight deer were 8 months of age and two were adults over 2 years in age. The average estimated body weight of the eight deer was 28 kg, but individually the deer ranged from 15.5 kg to 44.4 kg in weight. The six 8-month-old deer each received 0.5 ml of NalMed-A containing 30 mg nalbuphine hydrochloride, 10 mg azaperone tartrate, and 10 mg medetomidine hydrochloride per ml. The two adult deer received 1 ml of the same formulation. The average dose rate for the 8 month old deer, which averaged 22.6 kg in body weight, was 0.66 mg/kg nalbuphine hydrochloride, 0.22 mg/kg azaperone tartrate and 0.22 mg/kg medetomidine hydrochloride. The dose rate for the two adults, which averaged 44.4 kg in body weight, was 0.66 mg/kg nalbuphine hydrochloride, 0.22 mg/kg azaperone tartrate and 0.22 mg/kg medetomidine hydrochloride.

All eight deer were successfully sedated and immobilized. The average time to first effect was 2.3 minutes with a range of 1-4 minutes. The average time to sternal recumbency was 4.8 minutes with a range of 3-11 minutes. The average time to safe approach was 7.6 minutes with a range of 3-14 minutes. The core body temperatures averaged 101.5 F with no individual animal exceeding 102.7 F.

Approximately 15 minutes after safe approach, each deer was administered atipamezole hydrochloride IM at a dose rate of 5 mg of atipamezole hydrochloride for each mg of medetomidine hydrochloride in the initial sedative dose. All animals stood and walked away in an average of 9.6 minutes with a range of 4-14 minutes. All animals were observed for 24 hours for any after effects. None were observed.

Example 4

An immature, free-ranging mountain lion (*Puma concolor*) was successfully immobilized by the administration of NalMed for relocation to protect public safety. The mountain lion had an estimated weight of 20 kg. The animal received 0.5 ml of NalMed. The 0.5 ml dose contained 20 mg nalbuphine hydrochloride and 5 mg medetomidine hydrochloride. The dose rate was about 1.0 mg/kg of nalbuphine hydrochloride and 0.25 mg/kg medetomidine hydrochloride. The time to first effect was less than 5 minutes and the time to safe approach was slightly over 5 minutes.

Sedation was reversed with a combination of atipamezole hydrochloride, tolazoline hydrochloride, and naltrexone hydrochloride. The animal recovered to standing within 3 minutes and was completely recovered within 15 minutes. The mountain lion was held and observed for 4 days before release and showed normal behavior and appetite with no after effects.

Example 5

Fifty-one (51) free ranging white tailed deer (*Odocoileus virginianus*) in central Alabama were administered NalMed by remote injection dart. The 51 subjects consisted of 38 males and 12 females. Each milliliter of NalMed contained 40 mg of nalbuphine hydrochloride and 10 mg of medetomidine hydrochloride. The immobilizations were reversed by hand injection of atipamezole hydrochloride. All drugs were administered intramuscularly. The deer weighed between 40 pounds (17.77 kg) and 225 pounds (100.00 kg) with an average weight of 101 lbs (44.88 kg). The average doses of nalbuphine hydrochloride and metatomide hydrochloride were 44.8 mg (1 mg/kg) and 11.2 mg (0.294 mg/kg), respectively. The elapsed time from injection to the first observed effect ranged from 1 to 15 minutes and averaged 3.46 minutes. The elapsed time from injection to the animal going to sternal recumbency ranged from 4 to 19 minutes with an average elapsed time of 7.28 minutes. The elapsed time from injection to safe approach ranged from 5 to 20 minutes and averaged 8.64 minutes.

All animals achieved a state of complete relaxation (level 5) and a state that allowed complete ease of handling (level 5). Only three animals showed any erratic movement of the legs (slight paddling). After a period of complete immobilization ranging from 1 to 30 minutes the antagonist (reversal) drugs atipamezole hydrochloride and naltrexone hydrochloride were administered. The atipamezole hydrochloride (25 mg/ml) was administered at a ratio of 2 ml for every ml of the NalMed administered, resulting in an atipamezole hydrochloride/medetomidine hydrochloride ratio of 5:1, which is the optimum ratio for reversal of the sedation effects of the medetomidine hydrochloride in the administered NalMed formulation. The immobilization was fully reversed with deer able walk away in a range of 2 to 20 minutes after administration with an average time of 7.98 minutes.

Example 6

Thirty-nine (39) free ranging white-tailed deer (*Odocoileus virginianus*), consisting of 38 females and 1 male, were immobilized with NalMed-A. The body weights of these deer ranged from 85 lbs (37.7 kg) to 125 lbs (55.5 kg) and averaged 109 lbs (48.4 kg). Each milliliter of administered NalMed-A contained 40 mg nalbuphine hydrochloride, 10 mg of medetomidine hydrochloride and 10 mg of azaperone tartrate. The average dose of the NalMed-A formulation was 1.5 ml in volume with a average dose rate of each component of nalbuphine hydrochloride of 1.23 mg/kg, medetomidine hydrochloride of 0.30 mg/kg, and azaperone tartrate of 0.30 mg/kg. The resulting immobilizations were reversed with 3 ml of a formulation of 25 mg/ml of atipamezole hydrochloride resulting in an average dose rate of 1.54 mg/kg. All drugs were administered intramuscularly. The NalMed-A was administered by remote injection dart. The atipamezole hydrochloride reversal drug was administered by hand injection. The elapsed time from injection to the first observed effect ranged from 3 to 7 minutes and averaged 4.54 minutes. The time to sternal recumbency ranged from 5 to 15 minutes and averaged 9.18 minutes. The time to safe approach ranged from 5 to 23 minutes and averaged 12.46 minutes.

All of the deer achieved a complete state of immobilization. Only four deer showed any sign of movement with stimulation (insertion of a vaginal drug delivery device) The atipamezole hydrochloride (25 mg/ml) was administered at a ratio of 2 ml for every ml of NalMed-A administered. This resulted in an atipamezole hydrochloride/medetomidine hydrochloride ratio of 5:1. After administration of the atipamezole hydrochloride the time to first observed effect ranged from 2 to 10 minutes and averaged 4.48 minutes. The elapsed time from injection until the animals could walk away ranged from 5 to 18 minutes with an average of 10.57 minutes Example 7

Twenty five (25) free ranging black bears (*Ursus americanus*) in Colorado were immobilized with a NalMed formulation containing 40 mg nalbuphine hydrochloride, 10 mg azaperone tartrate, and 10 mg medetomidine hydrochloride in each milliliter. The immobilizations occurred as part of normal bear management programs. The bears were trapped in culvert traps and the drugs injected intramuscularly by jab poles. The group consisted of 15 males and 10 females with an average weight of 65.49 kilograms. The average volume of drug for each bear was 1.3 ml of NalMed. The mean dose rate of each component of NalMed was 0.81 mg/kg nalbuphine hydrochloride, 0.20 mg/kg medetomidine hydrochloride and 0.20 mg/kg azaperone tartrate. The mean time to induced immobilization was 16.16 minutes in this group of bears, and the range was from 10 to 23 minutes. The extent of immobilization was excellent in each case. Atipamezole hydrochloride (25 mg/ml) was used to reverse the immobilization and was administered by hand injection at a ratio of 2 ml for every ml of the NalMed formulation used to induce the immobilization. The time to reversal ranged from 7 to 36 minutes with a mean time to reversal of 19 minutes.

Example 8

One adult free ranging moose (*Alces alces*) was administered 1.7 ml of a NalMed formulation containing 40 mg nalbuphine hydrochloride and 10 mg medetomidine hydrochloride by intramuscular injection from a remote injection dart under free-ranging field conditions in Colorado. The moose was completely immobilized in 8 minutes.

A second adult moose was administered 1.7 ml of a NalMed-A formulation containing 40 mg nalbuphine hydrochloride, 10 mg medetomidine hydrochloride and 10 mg azaperone by intramuscular injection from a remote dart under free-ranging conditions in Colorado. This second moose was also completely immobilized in 8 minutes.

In both cases reversal was accomplished by administering atipamezole hydrochloride, and both moose were completely reversed in 8 minutes.

Example 9

A mountain lion (*Felis concolor*) weighting 90 lbs was administered 1 ml of NalMed containing 40 mg nalbuphine and 10 mg of medetomidine. The first signs of sedation were observed in 4 minutes after intramuscular injection by remote injection dart. The animal was completely immobilized in 6 minutes. The immobilization was reversed by administering atipamezole hydrochloride, and the first signs of recovery were observed in 1 minute. The animal was completely recovered in five (5) minutes.

Examples 10 and 11

Twelve white tailed deer (*Odocoileus virginianus*) maintained within the research facilities of Caesar Kleberg Wildlife Research Institute at Texas A and M University in Kingsville, Tex. where the subject of this controlled trial to study the effects of NalMed and NalMed-A on captive white tailed deer (*Odocoileus virginianus*). The 12 deer used in this study were of both sexes, each over 1 year of age, and had body weights of 45 to 90 kilograms. Each animal was identified by a unique permanent ear tag. Both NalMed and NalMed-A was tested on each animal. Individual deer were assigned study numbers and marked by ear tags. The deer were passed through a chute, weighed on an electronic scale and entered a lift-restraint system where they were temporarily restrained. Once restrained, NalMed was administered intramuscularly by hand injection from an individual trained and experienced in drug delivery. Each deer was returned to their individual pen immediately after injection. The time from injection to the time of return to the pen was less than one minute.

Once recumbent, each deer was assessed for adequate sedation prior to approach. Eye ointment was applied bilaterally to protect the cornea during immobilization, and each deer was blindfolded and hobbled, if necessary. Each deer was examined for injury and any deer not in right lateral recumbency was placed in that position. After approximately 20 minutes of anesthesia monitoring and data gathering, the deer were given the antagonist by intramuscular injection.

In order to eliminate the possibility of conspecific aggression, each deer was remained in its individual pen and observed for complete recovery until the day after the procedure, after which time the deer were returned to their social groups. After the first replicate, the study group was given a washout period of at least 14 days and the procedure was repeated using NalMed-A.

The data and observations made on each deer and procedure was (a) animal ID, sex, age, and body weight; (b) total dose of each drug given; (c) exact time administered; (d) the name of the investigator injecting the subject deer; (e) time to first effect; (f) time to sternal recumbency; (g) time to safe approach and handling; (h) temperature, pulse and respiration measurements in 5 minute intervals for 20 minutes of anesthesia; (i) evaluation of the quality of anesthesia by reference to the level of muscular relaxation (subjective on a scale of 1-5, with five being flaccid), the level of partial oxygenation $PO_2$ or similar assessment of tissue oxygenation, and the response to handling, if any; (j) the times, amounts and locations of administration of the antagonist; (k) the time to first effect of the antagonist; (l) time to head up or able to maintain sternal position; (m) time to be able to rise; (n) time to safely walk or run; and (o) observations at 4, 8, 12 and 24 hours after initial administration of NalMed or NalMed-A to detect any re-sedation or adverse effects.

The study was a cross-over design, using a repeated measures mixed model with treatment and sex of the deer as fixed independent variables. For physiology variables, time was also included since the anesthetized deer could be approached as a fixed, independent variable. Deer ID and date were random variables. When normality tests suggested residuals were not normally distributed, a natural log transformation was used to stabilize the distribution of the residuals and report back-transformed values. Back transformed least squared means are more analogous to a median as a measure of central tendency and confidence limits will not be symmetric about the mean. In order to minimize the likelihood of failing to report an effect when an effect actually exists, alpha=0.1 was used to establish significance instead of the traditional 0.05; however, P-values were reported so that the results can be interpreted with any alpha value.

This study demonstrated that both NalMed and NalMed-A produce a clinically acceptable immobilization in white tailed deer. Deer anesthetized with NalMed showed first effects 2.1 minutes sooner and became recumbent 2.9 minutes earlier than deer treated with NalMed, as shown in the following Table 1. There was no significant difference in time before the animals could be approached. While under anesthesia, body temperature and heart rate did not vary between the agonists, but respiration rate was generally greater for animals anesthetized with NalMed than NalMed-A. Even though the analysis suggested an interaction between treatment, sex, and time, there was no clear pattern other than that the respiration rate was greater for NalMed (Table 2). Oxygen saturation also interacted with treatment, sex, and time, but only at the 20 minute measurement point was there a difference between treatments, and males had the opposite response as females, and thus no clear pattern in differences between treatments was evident (Table 2).

Once the antagonist was given, deer that had been anesthetized with NalMed showed the first effect of the antagonist 1.9 minutes earlier, first raised their head 2.0 minutes earlier, and stood up 3.7 minutes earlier than deer anesthetized with NalMed-A (Table 1). There was an interaction between treatment and sex for time of first effect that indicated the difference between the NalMed and NalMed-A treatments was due to treatment differences between females, with no difference between treatments in males (Table 2). Deer first walked earlier when anesthetized with NalMed, but the result was not significant.

The following Table 1 shows a least square means and 95% confidence interval (CI) of variables related to the time (in minutes) for anesthesia to take effect, physiology parameters during anesthesia, and the time (in minutes) for actions of an antagonist administered.

TABLE 1

| Phase | Variable | Treatment | | | | |
| --- | --- | --- | --- | --- | --- | --- |
| | | NalMed | | NalMed-A | | |
| | | Mean | 95% CI | Mean | 95% CI | P-value |
| Anesthesia | 1st effect | 5.1 | 2.7-7.6 | 3.0 | 0.6-5.4 | 0.036 |
| | Recumbent* | 7.9 | 4.7-13.1 | 5.0 | 3.0-8.3 | 0.029 |
| | Approach | 15.6 | 4.6-26.7 | 12.2 | 1.3-23.1 | 0.170 |
| Physiology | Body temperature (F.) | 103.1 | 97.9-108.3 | 102.1 | 96.5-107.7 | 0.613 |
| | Respiration rate (/min)[a] | 34.5 | 27.4-41.6 | 24.5 | 17.7-31.3 | 0.013[a] |
| | Heart rate (/min) | 61.5 | 17.3-105.7 | 53.9 | 4.1-103.6 | 0.508 |
| | $O_2$ saturation (%)[b] | 71.3 | 23.5-119.2 | 70.6 | 16.9-124.3 | 0.869[b] |
| Antagonist | 1st effect[c] | 2.9 | 1.5-4.3 | 4.7 | 3.3-6.1 | 0.031[c] |
| | Head-up | 4.5 | 2.9-6.1 | 6.5 | 4.8-8.1 | 0.047 |
| | Stand* | 6.9 | 4.6-10.5 | 10.6 | 7.0-16.1 | 0.087 |
| | Walk* | 7.4 | 4.8-11.1 | 11.0 | 7.3-16.7 | 0.118 |

*variable log transformed for analysis and lsmeans back transformed for reporting
[a]treatment*sex*time interaction p-value = 0.060 (see Table 2 for results)
[b]treatment*sex*time interaction p-value = 0.032 (see Table 2 for results)
[c]treatment*sex interaction p-value = 0.075 (see Table 2 for results)

The following Table 2 shows the results from tests in Table 1 in which there was a significant (P<0.1) interaction involving treatment, either a treatment*sex or a treatment*sex*time interaction.

TABLE 2

| Variable | Sex | Time | Treatment | | | | |
| --- | --- | --- | --- | --- | --- | --- | --- |
| | | | NalMed | | NalMed-A | | |
| | | | Mean | 95% CI | Mean | 95% CI | P-value |
| Respiration rate | F | 0 | 39.3 | 29.0-49.6 | 23.3 | 13.0-33.6 | 0.008 |
| | | 5 | 29.8 | 19.5-40.1 | 22.0 | 11.7-32.3 | 0.167 |

TABLE 2-continued

| Variable | Sex | Time | Treatment | | | | P-value |
| --- | --- | --- | --- | --- | --- | --- | --- |
| | | | NalMed | | NalMed-A | | |
| | | | Mean | 95% CI | Mean | 95% CI | |
| | | 10 | 32.5 | 21.8-43.2 | 22.7 | 12.4-33.0 | 0.096 |
| | | 15 | 31.9 | 21.2-42.6 | 23.3 | 13.0-33.6 | 0.144 |
| | | 20 | 32.6 | 21.4-43.8 | 22.7 | 12.4-33.0 | 0.107 |
| | M | 0 | 34.1 | 21.8-46.4 | 28.0 | 16.7-39.3 | 0.356 |
| | | 5 | 48.1 | 35.8-60.4 | 27.6 | 16.3-38.9 | 0.004 |
| | | 10 | 25.6 | 13.3-37.9 | 27.0 | 15.7-38.3 | 0.831 |
| | | 15 | 35.6 | 23.3-47.9 | 23.8 | 12.5-35.1 | 0.081 |
| | | 20 | 35.1 | 22.8-47.4 | 24.8 | 13.5-36.1 | 0.125 |
| $O_2$ saturation | F | 0 | 73.2 | 48.9-97.5 | 71.7 | 45.0-93.6 | 0.678 |
| | | 5 | 71.1 | 47.3-94.9 | 70.7 | 50.0-98.6 | 0.736 |
| | | 10 | 70.5 | 46.7-94.3 | 74.5 | 39.0-87.6 | 0.460 |
| | | 15 | 69.9 | 46.1-93.7 | 74.5 | 40.2-88.8 | 0.578 |
| | | 20 | 91.9 | 68.1-115.7 | 76.7 | 42.0-90.6 | 0.010 |
| | M | 0 | 56.8 | 33.0-80.5 | 71.7 | 47.9-95.5 | 0.165 |
| | | 5 | 70.0 | 46.3-93.7 | 70.7 | 46.9-94.5 | 0.946 |
| | | 10 | 72.3 | 48.5-96.0 | 74.5 | 50.7-98.3 | 0.832 |
| | | 15 | 83.8 | 60.0-107.5 | 74.5 | 50.7-98.3 | 0.391 |
| | | 20 | 54.3 | 30.5-78.0 | 76.7 | 52.9-100.5 | 0.039 |
| 1$^{st}$ effect antagonist | F | n/a | 2.3 | 0.4-4.2 | 5.7 | 3.8-7.6 | 0.009 |
| | M | n/a | 3.4 | 1.3-5.5 | 3.8 | 1.7-5.9 | 0.716 |

The first, third, fifth, sixth, tenth and eleventh examples demonstrate the effectiveness of NalMed and NalMed-A on members of the mammalian family Cervidae, the second Example demonstrates the effectiveness of NalMed and NalMed-A on members of the mammalian family Bovidae, and the fourth and ninth examples demonstrate the effectiveness of NalMed on a carnivore species of the mammalian family Felidae. The eighth Example demonstrates the effectiveness of NalMed and NalMed-A on members of the mammalian family Cervidae, and the seventh Example demonstrates the effectiveness of NalMed on members of the mammalian family Ursidae.

From an overview perspective, NalMed and NalMed-A offers the significant benefit of freedom from governmental regulatory burden while still achieving acceptable sedation and immobilization in a wide range of non-domesticated mammalian species, including free-ranging individuals. The freedom from governmental regulation allows NalMed and NalMed-A to be used for the betterment of non-domesticated animals and the protection of public safety in circumstances where sedation or immobilization was not previously available, because a non-veterinarian may administer NalMed or NalMed-A immediately, and because the strict record-keeping and safekeeping regulations for controlled substances do not discourage use of NalMed and NalMed-A. NalMed and NalMed-A are reversed rapidly to prevent undue harm to free-ranging animals from natural causes after the immobilization event. NalMed and NalMed-A achieve sedation and immobilization which is comparable to known synergistic drug combinations, with no greater adverse side effects, at essentially no cost in terms of administrative burden and responsibility.

The significance of NalMed and NalMed-A and their improvements and advantages will become apparent upon gaining a full appreciation of the ramifications and improvements of the present invention. Preferred embodiments of the invention and many of its improvements have been described with a degree of particularity. The description is of preferred examples of implementing the invention, and is not intended to limit the scope of the invention. The scope of the invention is defined by the following claims.

The invention claimed is:

1. An injectable agent for sedating and immobilizing non-domesticated mammalian animals comprising a pharmaceutically effective combination of nalbuphine hydrochloride and medetomidine hydrochloride, wherein the combination is a liquid solution and the approximate relative weight ratio relationship of the pharmaceutically effective ingredients is 14-55 mg/ml of nalbuphine hydrochloride and 5-22 mg/ml of medetomidine hydrochloride.

2. An agent as defined in claim 1, wherein the approximate relative weight ratio relationship of the pharmaceutically effective ingredients is 40 mg/ml of nalbuphine hydrochloride and 10 mg/ml of medetomidine hydrochloride.

3. An agent as defined in claim 1, wherein the combination further includes azaperone tartrate.

4. An agent as defined in claim 3, wherein the relative weight ratio relationship of the pharmaceutically effective ingredients is 14-55 mg/ml of nalbuphine hydrochloride, 5-22 mg/ml of azaperone tartrate and 5-22 mg/ml of medetomidine hydrochloride.

5. An agent as defined in claim 3, wherein the approximate relative weight ratio relationship of the pharmaceutically effective ingredients is 40 mg/ml of nalbuphine hydrochloride, 10 mg/ml of medetomidine hydrochloride and 10 mg/ml of azaperone tartrate.

6. An agent as defined in claim 4, wherein an effective amount of the liquid solution is no more than 3 milliliters.

* * * * *